United States Patent [19]

Fujii et al.

[11] 4,094,609

[45] June 13, 1978

[54] HIGH SENSITIVITY ABSORPTIOMETER

[75] Inventors: Yoshio Fujii; Mitsuo Shimada, both of Katsuta; Sadabumi Ohnuma, Hitachi, all of Japan

[73] Assignee: Hitachi, Ltd., Japan

[21] Appl. No.: 767,888

[22] Filed: Feb. 11, 1977

[30] Foreign Application Priority Data

Feb. 19, 1976 Japan .................................. 51-17423

[51] Int. Cl.² ........................................ G01N 21/22
[52] U.S. Cl. ...................................... 356/201; 353/52
[58] Field of Search ............... 356/201, 204, 205, 206, 356/208; 353/52

[56] References Cited

U.S. PATENT DOCUMENTS

| 2,033,038 | 3/1936 | Lee | 353/52 |
| 3,730,627 | 5/1973 | Kent | 356/205 |
| 3,778,162 | 12/1973 | Gant et al. | 356/206 |

FOREIGN PATENT DOCUMENTS

| 856,617 | 12/1960 | United Kingdom | 356/208 |

Primary Examiner—John K. Corbin
Assistant Examiner—R. A. Rosenberger
Attorney, Agent, or Firm—Craig & Antonelli

[57] ABSTRACT

A high sensitivity absorptiometer comprises a light source lamp accompanied inevitably with heat generation, a sample container through which the light from the light source is transmitted and a detector device for detecting the light which has transmitted through the sample container. The light emitted from the light source lamp and directed to the sample container is adapted to pass through a chamber which is formed fluid-tight on a surface portion of the light source lamp or through a solid state optical conductor such as optical fiber having a light inlet end face closely fitted to the surface portion of the lamp, thereby to suppress movement and turbulence of air as caused by heat generated by the light source lamp with a view to excluding noise and drift ascribable to the air movement or turbulence phenomenon from the signal obtained from the detector device.

18 Claims, 7 Drawing Figures

HIGH SENSITIVITY ABSORPTIOMETER

BACKGROUND OF THE INVENTION

This invention relates in general to an absorptiometer and in particular to a high sensitivity absorptiometer which is especially suited for detecting a component contained in a sample to be detected with a high detection sensitivity.

In these years great progress has been made in the field of absorptiometer and there are available various high sensitivity absorptiometer with a low noise and reduced drift. Such reduced noise and drift characteristics have been accomplished to a certain degree through attempts for developing a stabilized electric power source for a light source and improving a signal processing system such as electronic amplifier circuits or the like. However, there are demand for an absorptiometer with a more enhanced sensitivity, as an increased accuracy is required in the measurement and analysis in the associated field such as liquid chromatography.

Among the causes for the generation of noise and drift which can not be eliminated by electric or electronic circuitries, there may be enumerated a movement or flow of a sample in the application where the sample containing or accommodating means is composed of a flow cell. It has, however, been found that there still exist other causes for the noise and the drift, even after the problem due to the sample flow has been solved.

In this connection, it is to be noted that the light source chamber as well as the sample containing means chamber of the hitherto known absorptiometer are opened to the exterior with a view to obtaining a good ventilation. In general, the light emitting source of the absorptiometer will at the same time constitute a heat generating source. Accordingly, when the light emitting source is exposed to the atmosphere, ambient air around the light source will be thermally expanded due to the thermal conduction, radiation and convection of heat generated by the hight source. Such movement of air of course involves additional air flow and gives rise to irregular movements of air, i.e. a so-called air turbulence phonomenon.

The inventors of the present application have found in the course of study for developing a high sensitivity absorptiometer that occurrence of the air turbulence or movements in the optical system of the absorptiometer will cause light beams passing there through to be refracted irregularly thereby to bring about changes in the light quantity impinging onto the photo-detector, which in turn provides a cause for the noise and the drift of the detected signals. Heretofore, no report has been made on such adverse influence of air movement or turbulence phenomenon.

SUMMARY OF INVENTION

In order to effectively suppress the air movement or turbulence in the light path of absorptiometer, a space which is located adjacent to the light source and through which the light beam extracted from the light source are transmitted is shielded from the ambient environment. Furthermore, it will be appreciated that the measurement or analysis accuracy may be much more enhanced by maintaining a light transmitting chamber at a constant temperature and/or by substantially evacuating the chamber.

Accordingly, an object of the invention is to provide a high sensitivity absorptiometer in which noise and/or drift due to the air movement and turbulence in the light path of the absorptiometer as caused by heat generated from a light source lamp are significantly decreased.

According to an aspect of the invention, a chamber which is inhibited from fluid communication with the ambient exterior or atmosphere is provided on a surface portion of a light source lamp in a fluid-tight manner. The light emitted from the source lamp is made to pass through the tightly fitted chamber before reaching the sample containing cell.

According to another aspect of the invention, a light inlet or input end face of a solid state optical conductor such as an optical fiber is positioned in contact with or in the close vicinity of the surface of the light source lamp. The light is then directed to the sample containing cell through the optical conductor.

The above and other objects, features and advantages of the invention will become more apparent from the description of preferred embodiments of the invention taken in conjunction with the accompanying drawings.

DETAILED DESCRIPTION OF THE PREFERRED EMBODIMENTS

Figure 1:
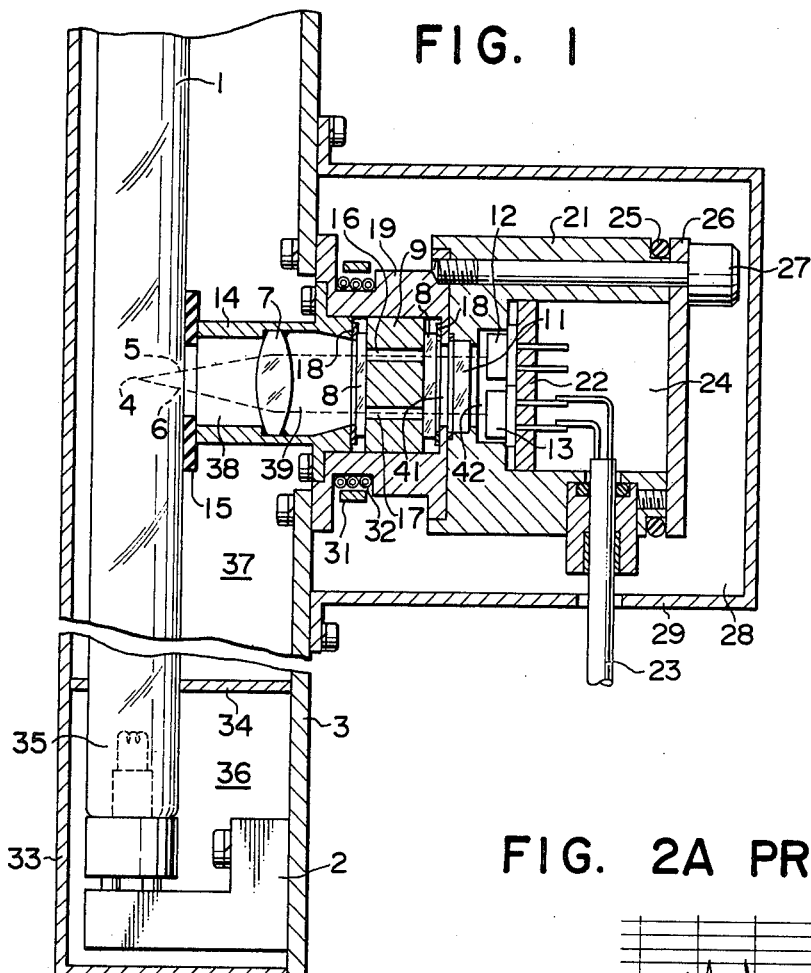
FIG. 1 is a longitudinal sectional view showing an absorptiometer according to an embodiment of the invention.

Referring to FIG. 1, a mercury-arc lamp 1 of a low pressure type is fixedly mounted on a base plate 3 constituting a part of a fluid-tight chamber by means of a lamp supporting member or socket 2. Light beams 5 and 6 assumed as emitted from a light extracting portion 4 located at a middle portion of the mercury-arc lamp 1 are collimated by a collimator lens 7 and subsequently pass through a flow cell composed of a cell body 9 and a cell window 8. The light beams which have passed through the flow cell will then impinge on detector elements 12 and 13 after having passed through an optical filter 11. The lens 7 is tightly in a light path cylinder 14 which is made of a material having a high thermal conductivity such as aluminium, copper or the like and which provides a light path. The cylinder 14 is closely fitted onto a glass bulb surface of the mercury-arc lamp 1 through a sealing member 15 provided at the abutting end of the cylinder. The cell window 8 is made of a quartz glass and welded to the opaque cell body 9 which in turn is formed with flow passages 16 and 17 through which a fluid or liquid to be measured is caused to flow. The flow cell is coupled to a cell holder 19 and the light path cylinder 14 through a packing 18. The filter 11 destined to take out the monochromatic light is secured to a detector block 21. A pair of detector elements 12 and 13 are secured to the detector block 21 by means of a fitting plate 22 and electrically connected to a lead wire cable 23. A chamber 24 is formed in the detector block and maintained in a fluid-tight state by means of an O-ring 25 and a cover 26 secured by set screws 27. The detector block 21 as well as the cell holder 19 are enclosed by a cover 29 which also serves to define a chamber 28. A spiral metal pipe 32 having several turns is securedly held by a stationary plate 31 and functions to balance the temperature of liquid flowing into the flow cell with that of the cell body 9. A partition plate 34 located in a chamber defined by the base plate 3 and a cover 33 shields the light extracting portion 4 of the source lamp from a heat generating portion 35 located in the vicinity of the lamp filament.

In the structure described above, it will be understood that the portion of the mercury-arc lamp at which the highest temperature prevails is the heat generating portion 35 where the filament is located and the enclosing chamber 36 is subjected to the highest temperture. The partition plate 34 serves to reduce or suppress the heat transfer from the chamber 36 to the chamber 37. The chamber 37 is located so as to enclose exteriorly the light extracting portion 4 and subjected to a high temperature next to that of the chamber 36. The chamber 38 formed by the light path cylinder 14 and a lens 7 is tightly or closely fitted to the bulb glass surface of the mercury-arc lamp 1 by means of the sealing member 15 which may be formed of left or like material. The light path cylinder 14 is tightly fitted to the lamp surface to such degree that no gas flow may occur relative to the ambient exterior or atmosphere when the chamber 38 is at a normal pressure. In this connection, it is to be noted that the tight or close fitting of the chambers to the lamp surface which are inhibited from fluid communication with the exterior may be accomplished by directly closs-fitting the abutting ends of such chambers to the lamp surface or by closely fitting the end portions of such chamber to a supporting base portion formed integrally with the mercury-arc lamp. The chamber 39 located adjacent to the chamber 38 is maintained in a fluid-tight state at a normal pressure by means of the lens 7, cell window 8 and the light path cylinder 14. Both chambers 41 and 42 are also fluid-tight closed so that fluid flow from or to the exterior is inhibited.

In the above described embodiment, all the portions which constitute the light path extending from the light extracting portion of the source lamp to the detector elements are shielded from the ambient atmosphere. However, it will be appreciated that the portions which have negligible temperature difference relative to the ambient temperature such as the chambers 41 and 42 may be opened to the exterior because of their not incurring any appreciable increase of noise.

In the case of the above described embodiment, each of the chambers 38, 39, 41 and 42 is placed in a tightly closed box so that these chambers are immune to the influence of the ambient temperature. In more particular, the chambers 38 and 39 are surrounded by the chamber 37, while the chambers 41 and 42 are housed in the chamber 28. This arrangement is effective to decrease the temperature difference relative to the ambient temperature, whereby the drift is especially reduced. Since each of the chambers 38, 39, 41 and 42 is of a relatively small volume, a uniform temperature distribution will be likely to occur in the respective chambers. As a result, gas flow or movements will scarcely take place in these chambers.

By virtue of the fact that the light path cylinder 14 is formed of a material having a high thermal conductivity, the chambers 38 and 39 are brought to a balnanced state in respect of the temperature in a short time, involving additionally an excellent heat radiation effect.

Figure 2A:
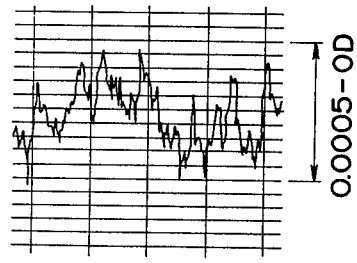
FIGS. 2A and 2B graphically illustrate noises contained in the detection signals obtained by a hitherto known absorptiometer and an absorptiometer according to the invention, respectively.
Figure 2B:
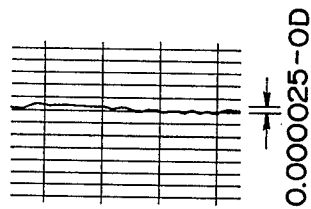

FIGS. 2A and 2B illustrate magnitude of noise produced in the apparatus according to the invention in comparison with the noise produced in a prior art apparatus. More specifically, FIG. 2A graphically illustrates the results of measurement performed by the prior art apparatus in which the light path cylinder 14, the partition plate 34 and the cover 33 are not provided. It can be seen that the light absorbance change of the base line amounts to about 0.0005 Absorbance Units. On the contrary, the absorbance change of the base line is decreased to 0.000025 Absorbance Units in the case of the measurement carried out by the apparatus shown in FIG. 1, as will be seen from FIG. 2B. In reality, the magnitude of noise shown in FIG. 2B is decreased to 1/20 of the noise shown in FIG. 2A. In either case, the measurement has been carried out by flowing methyl alcohol through a sample cell at a flow rate of 1.0 ml/min by means of a reciprocating piston pump.

Figure 3:
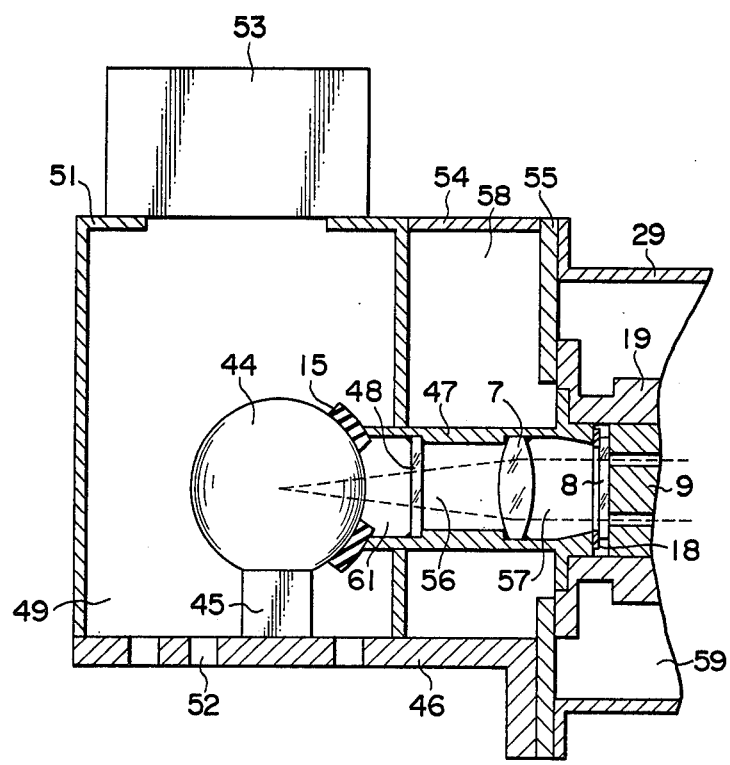
FIG. 3 shows schematically a main portion of another embodiment of the invention in a sectional view.

FIG. 3 shows another embodiment of the invention in which a tungsten lamp 44 is employed as a light source. The tungsten lamp 44 is secured to a lamp base 46 by means of a lamp socket 45. The light emitted from the lamp 44 passes through a heat shielding plate 48 which is provided in a light path cylinder 47 and constituted by an infrared ray absorbing filter of phosphate glass and a lens 7 and the light reaches a flow cell body 9. The lamp chamber 49 is formed by a cover 51 and the base 46 and has a vent hole 52 through which either natural ventilation or enforced heat-radiating ventilation through a fan 52 is effected, as occasion requires. The partition wall 54 in combination with the light path cylinder 47 and the base plate 55 defines a chamber 58 which serves to decrease the temperature difference between the chambers 56; 57 and the ambient atmosphere. The flow cell is accommodated within a chamber 59. In FIG. 3, other components or parts similar to those of FIG. 1 are indicated by the same reference numerals.

In the case of the above described embodiment, each of the chambers 61, 56 and 57 through which the light beams are transmitted is constructed in a tightly closed manner independently from one another. Since the temperatures in the individual chambers are in a balanced state, the air flows in the chambers can be suppressed at a minimum. The light path cylinder 47 which also forms an exteriorly shielded chamber 61 in cooperation with the heat-shielding plate 48 is closely attached to the glass surface of the tungsten lamp 44 through a resilient seal 15.

In general, the tungsten lamp has the heat generating portion at the same location as the light extracting portion and generates a relatively large quantity of heat. Accordingly, ambient air of the lamp will tend to more most easily under the influence of heat. In order to evade such phenomenon, the chamber 61 is maintained in a substantially tightly closed state with the aid of a seal made of a heat-resisting glass wool. The interior of the lamp 44 should preferably be evacuated thereby to prevent gas movement within the lamp 44.

In the above described embodiment, since the light path is constituted by a plurality of the tightly closed and partitioned chambers, the temperatures in the individual chambers are independently balanced thereby to prevent any fluid movement in the chambers. This structure is also effective to reduce the noise and drift remarkably.

Figure 4:
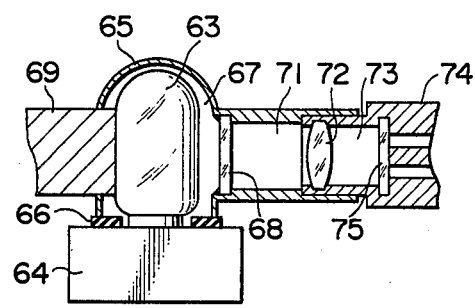
FIG. 4 shows schematically in a sectional view a main portion of still another embodiment of the invention.

FIG. 4 shows still another embodiment of the invention. Lamp 63 is supported on a supporting mount 64. A cover 65 is located so as to enclose the lamp 63 with the space between the cover 65 and the surface of the lamp 63 which is selected to be very narrow. The end portion of the cover 65 is tightly fitted to the supporting mount 64 through a sealing member 66. A first closed chamber 67 tightly closed from the exterior is formed by a cover 65 and a shield plate 68. It should be noted that the lamp 63 as well as the cover 65 are positioned in contact with a cooling block 69 which is adapted to be cooled by an appropriate coolant. A second closed chamber 71 is formed by a shield plate 68, lens 72 and the cover 65. Further, a third closed chamber 73 is formed by the lens 72, the cell body 74 and the cell window 75.

The embodiment shown in FIG. 4 provides similar advantages as those of the preceding embodiments. Gas flow into the first closed chamber 67 from the exterior is positively prevented. Additionally, since the chamber 67 is so formed that the interior space thereof is made extremely small, movement of gas within the chamber 67 is essentially suppressed.

Figure 5:
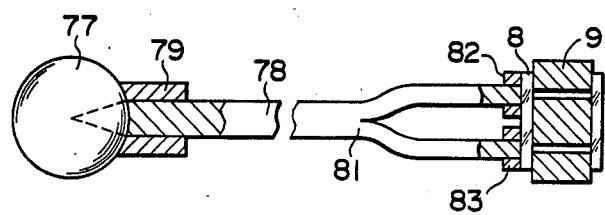
FIG. 5 shows schematically a further embodiment of the invention in a frequental sectional view.

FIG. 5 shows a further embodiment of the invention. A light source lamp 77 is closely attached with an optical fiber 78 at the balb surface thereof by means of an end face fitting device 79. The optical fiber 78 is divided at a branching point 81 and each of the divided branches of the optical fiber is secured to the cell window 8 of the cell body 9 by means of respective end face fitting devices 82 and 83. Since the light emitted from the light source is directly guided to the cell window 8 through a solid state optical conductor or the optical fiber without passing through chambers in which air is present, influence of air movements as caused by the heat generated from the light source is completely eliminated, whereby noise and drift are sharply decreased. It is also possible within the scope of the invention to connect optically the end face of the optical fiber to the light source through a chamber which is inhibited from fluid communication with the exterior.

Figure 6:
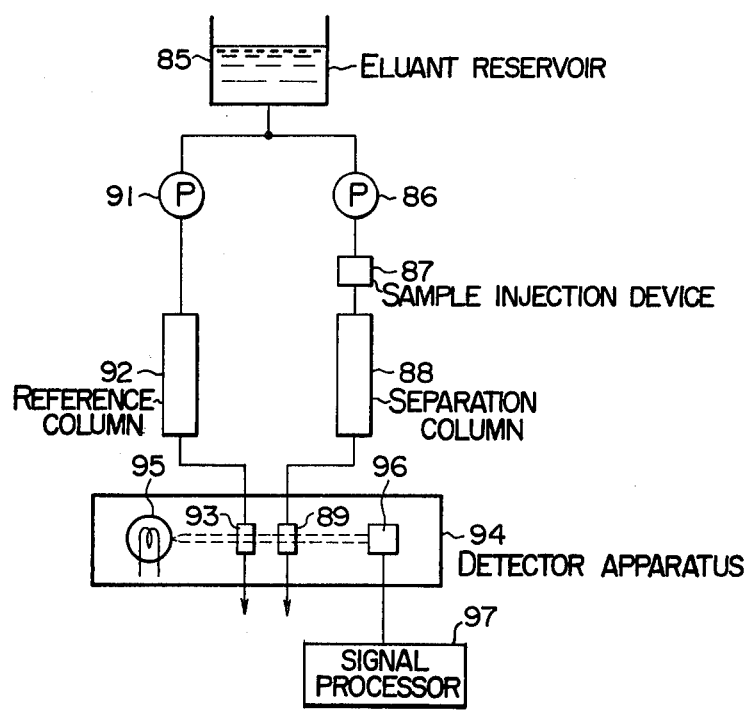
FIG. 6 is a block diagram showing a liquid chromatographic system to which the invention can be applied.

Finally, referring to FIG. 6, description will be made on a liquid chromatography in which a high sensitivity absorptiometer according to the invention is utilized as a detector for the chromatography. An eluting solution contained in an eluent reservoir 85 is caused to flow through a sample flow path and a reference flow path. The sample flow path is composed of a pump 86, a sample injection device 87, a separation column 88 and a sample flow cell 89. On the other hand, the reference flow path includes a liquid feeding pump 91, a reference column 92 and a reference flow cell 93. The detector apparatus 94 includes a sample flow cell 89 through which effluent from the separation column 88 is caused to pass, a reference flow cell 93 through which elute from the reference column 92 is caused to pass, a light source 95 for illuminating both of the flow cells 89 and 93 and a photodetector 96 for sensing the light beams transmitted through the flow cells 89 and 93. It will be appreciated that the flow cells 89 and 93 correspond, respectively, to the flow passages 16 and 17 composed of the cell body 9 and the cell window 8 as shown in FIG. 1. Output signals from the photodetector 96 are processed by a suitable signal processor 97. It has been ascertained that the liquid chromatographic system of the structure described above and incorporating an absorptiometer according to the invention allows analysis with an extremely high accuracy.

We claim:

1. A high sensitivity absorptiometer comprising a light source lamp with an inevitable heat generation, sample containing means through which light from said light source lamp transmits, detecting means for detecting the light transmitted through said sample accommodating means, and a chamber formed by at least a surface portion of said light source lamp and an enclosing wall member fitted tightly to said surface so that said chamber is inhibited from fluid communication with the exterior, wherein said light emitted from said light source lamp and directed to said sample containing means is caused to pass through said chamber.

2. An absorptiometer as set forth in claim 1, wherein said chamber is formed by a surface portion of said light source lamp, an enclosing wall member tightly fitted to said surface and a light collecting lens mounted fluid-tight onto said enclosing wall member.

3. An absorptiometer as set forth in claim 1, wherein said chamber is formed by a surface portion of said light source lamp, an enclosing wall member closely fitted to said surface portion, and a light transmissive heat-shield member mounted fluid-tightly on said enclosing wall member.

4. An absorptiometer is set forth in claim 1, wherein said enclosing wall member is made of a material having a high thermal conductivity.

5. An absorptiometer as set forth in claim 1, wherein a plurality of chambers are provided between said light source lamp and said sample containing means, each of said chambers being enclosed by said enclosing wall member and partitioned from one another by light transmissive members so that said chambers are inhibited from fluid communication with ambient exterior, and wherein said light emitted by said light source lamp is guided to said sample containing means through said partitioned individual chambers.

6. An absorptiometer as set forth in claim 5, wherein at least one of said light tansmissive members is composed of a heat shielding element.

7. An absorptiometer as set forth in claim 5, wherein a space between said sample containing means and said detecting means is defined by a chamber closed fluid-tight from the ambient exterior.

8. An absorptiometer as set forth in claim 1, wherein said chamber is accommodated within a fluid-tight closed chamber.

9. An absorptiometer as set forth in claim 1, wherein said chamber and said sample containing means are housed within a fluid-tight closed chamber.

10. An absorptiometer as set forth in claim 1, wherein said chamber is housed within a first fluid-tight chamber and said sample containing means is housed within a second fluid-tight chamber.

11. An absorptiometer as set forth in claim 7, wherein all of said chambers are housed within at least one fluid-tight chamber.

12. An absorptiometer as set forth in claim 1, wherein said chamber is maintained at a lower pressure than the atmospheric pressure.

13. An absorptiometer as set forth in claim 1, including means for maintaining said chamber at a constant temperature.

14. An absorptiometer as set forth in claim 1, wherein said sample containing means is composed of a flow cell.

15. An absorptiometer as set forth in claim 1, wherein a pipe through which a liquid to be detected passes is thermally conductively contacted to a member which is thermally conductively coupled to said sample containing means.

16. An absorptiometer as set forth in claim 14, wherein said absorptiometer is used as a detector for a liquid chromatography.

17. A high sensitivity absorptiometer comprising a light source lamp with an inevitable heat generation, sample containing means through which light from said light source lamp is caused to pass, an optical fiber having a light input end face positioned in contact with a surface portion of said light source lamp and serving to guide the light from said light source lamp to said sample containing means, and detecting means for detecting light transmitted through said sample containing means.

18. A high sensitivity absorptiometer comprising a light source lamp with an inevitable heat generation, sample containing means through which light emitted from said light source lamp is caused to pass, detecting means for detecting light transmitted through said sample containing means, an optical fiber for guiding the light from said light source lamp to said sample containing means, and a fluid-tight chamber formed by at least a surface portion of said light source lamp, an enclosing wall member closely fitted to said surface portion and a light input end face of said optical fiber.

* * * * *